United States Patent [19]

Ishimura et al.

[11] Patent Number: 4,857,469
[45] Date of Patent: Aug. 15, 1989

[54] PROCESS FOR PREPARING OPTICALLY ACTIVE MERCAPTO COMPOUND

[75] Inventors: Fumihiro Ishimura; Satoru Ishikawa, both of Ohito; Seiji Akiyama, Shizuoka, all of Japan

[73] Assignee: Toyo Jozo Co., Ltd., Ohito, Japan

[21] Appl. No.: 171,380

[22] Filed: Mar. 21, 1988

[30] Foreign Application Priority Data

Apr. 9, 1987 [JP] Japan ................. 62-087744

[51] Int. Cl.$^4$ ............................................. C12P 41/00
[52] U.S. Cl. ................................... 435/280; 435/138
[58] Field of Search ............................ 435/130, 280

[56] References Cited

PUBLICATIONS

Abstract of Japanese Patent–J60256391-A, Dec. 1985.

Primary Examiner—Sam Rosen
Attorney, Agent, or Firm—Oblon, Spivak, McClelland, Maier & Neustadt

[57] ABSTRACT

A process for preparing an optically active mercapto compound having asymmetrical centers having the formula:

$$HS-(CH_2)_n-\overset{R_1}{\underset{|}{C^*H}}COOR \qquad [A]$$

in which $R_1$ represents an alkyl group, R represents a hydrogen atom or an alkyl group, C* represents an asymmetric carbon, n represents the value of 1 or 2, is disclosed. The process involves the reaction of a cultured microorganism having the ability of asymmetrically hydrolyzing ester bonds of the raw material, thus eliminating the need for protecting free mercapto groups which are unstable in the reaction conditions. The optically active mercapto compound is useful as a raw material for producing a compound having medicinal effects such as antihypertensive activity.

6 Claims, No Drawings

PROCESS FOR PREPARING OPTICALLY ACTIVE MERCAPTO COMPOUND

BACKGROUND OF THE INVENTION

1. Field of the Invention

This invention relates to a process for preparing an optically active mercapto compound having the following formula [A]:

$$\text{HS}-(\text{CH}_2)_n-\underset{|}{\overset{R_1}{C^*}}\text{HCOOR} \qquad [A]$$

in which $R_1$ represents an alkyl group, R represents a hydrogen atom or an alkyl group, $C^*$ represents an asymmetric carbon, n represents the value of 1 or 2.

The optically active mercapto compound prepared by the process of this invention is useful as a raw material for producing a medicinal compound, and specifically for producing a compound having medicinal effects such as antihypertensive activity.

2. Prior Art and Background of the Invention

Conventionally known processes for preparing the compound represented by formula [A] are (1) a process utilizing an optical resolving reagent (Japanese Patent Laid-open Nos. 151,912/1979 and 38,386/1980), and (2) a process for preparing this compound by reacting an optically active halogenated compound with a hydrosulfide which is obtained from hydrogen sulfide and a base (Japanese Patent Laid-open No. 38,768/1982).

The process utilizing an optical resolving reagent, however, requires a large amount of expensive resolving reagent for preparing optically active mercapto compound. The process has further disadvantages in that the product tends to contain the resolving reagent as an impurity and the resolving step is complicated. Thus, this is not necessarily a satisfactory process for industrially producing optically active mercapto compounds. The process disclosed in Japanese Patent Laid-open No. 38,768/1982 requires an optically active halogenated compound as an essential raw material, and cannot be applied where a mercapto compound is used as a raw material.

There are also known in the art processes for preparing optically active carboxylic acids or asymmetric esters by the action of enzymes, culture broth of microorganisms, bacterium, or bacterium-treated substances (Japanese Patent Laid-open No. 94,091/1985, Japanese Patent Laid-open No. 141,297/1985, and Japanese Patent Laid-open No. 256,391/1985). These processes, however, require a procedure for protecting thiol groups. In case where the intended product is a optically active mercapto carboxylic acid, the processes further requires, in addition to the procedure for protecting thiol groups, a step for eliminating the thiol groups. These drawbacks make it difficult to produce such optically active compounds inexpensively and efficiently.

The present inventors have made extensive studies on the process for preparing either d- or τ-isomer of carboxylic acid, or asymmetric carboxylic acid esters by asymmetrical hydrolysis of mixtures of carboxylic acids having d- and τ-isomers of mercapto groups, using fermentation engineering technique and with industrially acceptable efficiency. As a result, the inventors found that an optically active mercapto compound could be prepared with good efficiency without protecting free mercapto groups which is usually unstable in the reaction conditions.

SUMMARY OF THE INVENTION

Accordingly, an object of this invention is to provide a process for preparing an optically active mercapto compound having the following formula [A]:

$$\text{HS}-(\text{CH}_2)_n-\underset{|}{\overset{R_1}{C^*}}\text{HCOOR} \qquad [A]$$

in which $R_1$, R, $C^*$, and n have the same meanings as defined above; which comprises using, as a raw material, a compound represented by the following formula [B]:

$$\text{HS}-(\text{CH}_2)_n-\underset{|}{\overset{R_1}{\text{CH}}}\text{COOR}_2 \qquad [B]$$

in which $R_2$ represents an alkyl group, $R^1$ and n have the same meanings as defined above; having a cultured microorganisms or its treated substance acted on said compound of formula [B], said cultured microorganism or its treated substance having ability of asymmetrically hydrolyzing ester bonds of said compound of formula [B]; and separating said compound of formula [A] from the resulting mixture.

Other and further objects, features and advantages of the invention will appear more fully from the following description.

DETAILED DESCRIPTION OF THE INVENTION AND PREFERRED EMBODIMENTS

The compound of formula [B] which is the starting raw material of this invention is a mixture of the d- and τ-isomers. Specifically, they are α-methyl-β-mercaptopropionic acid methyl ester, α-methyl-β-mercaptopropionic acid ethyl ester, 2-ethyl-4-mercaptobutanoic acid methyl ester, 2-ethyl-4-mercaptobutanoic acid ethyl ester, 2-(mercaptomethyl)butanoic acid methyl ester, 2-(mercaptomethyl)butanoic acid ethyl ester, and the like. There is no specific limitation as to the proportion of the d- and τ-isomers of these esters. These compounds are known compounds which can be available as they are, or can be readily prepared by methods known in the art.

Microorganisms which have the ability of asymmetrically hydrolyzing the ester bonds of the compounds of formula [B] include those belonging to the genuses Rhodotorula, Microbacterium, Bacillus, Alcaligenes, Flavobacterium, Acinetobactor, Pseudomonas, Candida, Caulobacter, Sporidiobolus, Cryptococcus, Trichosporon, Rhodosporidium, Sporobolomyces, and the like. Specifically, preferred microorganisms are either members selected from the group consisting of *Rhodotorula glutinis, Rhodotorula minuta, Microbacterium lacticum, Bacillus laterosporus, Alcaligenes faecalis, Pseudomonas piscicida, Flavobacterium ferrugineum, Acinetobactor lwoffii, Candida utilis, Caulobacter crescentus, Sporidiobolus johnsonii, Cryptococcus laurentii, Cryptococcus albidus, Trichosporon cutaneum, Rhodosporidium toruloides, Sporobolomyces albo-rubescens*, as well as variants of these microorganisms and those derived from these microorganisms by gene manipulation or cell fusion. Given as specific strains of these microorganisms are *Rhodotorula glutinis* IFO 0389, *Rhodotorula minuta* IFO 0387, *Microbacterium lacticum* ATCC 8180, *Bacillus laterosporus* ATCC 64, *Alcaligenes faecalis* ATCC 15246, *Pseudomonas piscicida* ATCC 15251, *Caulobacter crescentus* ATCC 19089, *Flavobacterium ferrugineum* ATCC 13524, *Acinetobactor lwoffii* ATCC 21284, *Candida utilis* ATCC 9226, *Sporidiobolus johnsonii* IFO 6903, *Cryptococcus laurentii* ATCC 18803, *Cryptococcus albidus* IFO 1320, *Trichosporon cutaneum* IFO 0173, *Rhodosporidium toruloides* NRRL Y-1019, *Sporobolomyces alborubescens* NRRL Y-6683, and the like.

Culture product of microorganisms used in the process of this invention are, for example, cultured bacterial bodies of the above-mentioned microorganisms and/or culture broth of these microorganisms. Treated substances of microorganisms are treated substances of cultured bacterial bodies of the above-mentioned microorganisms and/or culture broth of these microorganisms. More specifically, treated cultured bacterial bodies include dried bacterial bodies, for example, freeze-dried or spray-dried bacterial bodies, bacterial bodies treated by an organic solvent such as acetone, toluene, or the like, crushed bacterial bodies, extracted bacterial bodies, immobilized substances, and the like.

Treated cultured bacterial bodies and/or treated culture broth of these microorganisms are, for example, enzyme or its treated substances which are obtained by treating the cultured bacterial bodies and/or the culture broth of these microorganisms, and capable of acting on the compound of formula [B] and asymmetrically hydrolyzing ester bonds of this compound. These enzymes are usually called esterase, and broadly designate the esterase, including lipase having an activity on a water-insoluble ester substrate.

Various methods generally employed in collecting enzymes from microorganisms may be used for extracting these enzymes. One example of such methods of extraction is that described in "KOSO KENKYUSHO" vol. 1, Shiro Akabori (1955). Isolation and purification of the enzymes asymmetrically hydrolyzing ester bonds of the compound of formula [B] are also carried out according to the method described in "KOSO KENKYUSHO" and other methods reported in various literatures. The treated substances of these enzymes include dried enzymes obtained, for example, by freeze-drying or spray-drying, or the immobilized substance, and the like.

The immobilized substances of the microorganisms or enzymes include the immobilized microorganisms or enzymes. Any immobilized substances which can sustain the continuous reaction with the ester substrate can be employed in the practice of this invention. Specific examples of the immobilized microorganisms or enzymes include, for example, those carried on a water-insoluble carrier, including polysaccharides and their derivatives such as cellulose and agarose, and porous glass; bridged to a bridging agent such as glutaraldehyde; or encapsuled in a synthetic polymeric compound such as polyacrylamide gel, polyvinyl alcohol gel, or photo-curable resin, or in a natural polymeric compound such as starch, carageenan, or casein gel.

According to the process of this invention, the reaction is carried out at a concentration of the raw material, the compound of formula [B], in the reaction mixture, of usually 0.5–40% (v/v), and preferably 1.0–5.0%. (v/v). Water or a buffer solution, such as phosphate buffer, is used for the reaction medium. When a microorganism or its treated substance is used in the reaction, the amount to be added is 0.1–10 U/ml, preferably 1–5 U/ml, in terms of the esterase activity possessed by the microorganisms or its treated substance. When an enzyme or its treated substance is used, the amount to be added is 0.1–10 U/ml, preferably 1–5 U/ml, in terms of the esterase activity possessed by the enzyme or its treated substance. The reaction is carried out at a temperature in the range of −15° to 70° C., preferably −5° to 40° C. When the reaction is carried out at below a water freezing point, a water soluble organic solvent such as methanol, ethanol, DMSO, or the like is added as required. The reaction is effected for 1–24 hours, preferably 2–10 hours, at a pH range of 5–10, preferably 6–9. For adjusting the pH range, in order to offset the decrease of the pH value due to production of carboxylic acid in the course of the reaction, neutralizing agent such as sodium hydroxide, potassium hydroxide, sodium carbonate, or the like may be added from time to time as the reaction proceeds.

Separation or purification of the product from the reaction mixture can be carried out by means of known methods such as, for example, extraction, column chromatography, distillation, or the like. When separation of microorganisms is involved, centrifugation, for example, is employed for separating microorganisms from the reaction medium.

Other features of the invention will become apparent in the course of the following description of the exemplary embodiments which are given for illustration of the invention and are not intended to be limiting thereof.

EXAMPLES

EXAMPLE 1

(1) A culture medium in the amount of 1,000 ml, comprising 2% of glucose, 0.5% of peptone, 0.3% of malt extract, and 0.3% of yeast extract and of a pH of 6.0 was sterilized. The strain *Rhodotorula glutinis* IFO 0389 was inoculated to the culture medium and cultured at 28° C. for 70 hours. The culture broth was centrifuged to collect the microorganism, to which 50 ml of physiological saline was added to obtain a suspension of the microorganism.

(2) All the suspension liquid of the microorganism prepared in (1) above was added to 1,000 ml of water containing 10 gm of d$\tau$-$\alpha$-methyl-$\beta$-mercaptopropionic acid methyl ester. The mixture was adjusted to pH 7.0 using 2N sodium hydroxide aqueous solution, and reacted at 30° C. for 20 hours. After the reaction, the microorganism was removed from the reaction mixture by centrifugation, and $\alpha$-methyl-$\beta$-mercaptopropionic acid methyl ester remaining unhydrolyzed in the filtrate was extracted using 400 ml of ethyl acetate. This extraction procedure was repeated using using the same amount of ethyl acetate. From the both ethyl acetate phases ethyl acetate was removed under a vacuum, and the residue was subjected to distillation at 8 mmHg to collect the fraction distilled at a temperature range of 52°–54° C. The fraction was optically active $\alpha$-methyl-$\beta$-mercaptopropionic acid methyl ester 3.2 gm $\{[\alpha]_D^{25} = -33 \ (C=1.05 \ \text{methanol})\}$. The compound was identified by $C^{13}$ NMR, H-NMR, infrared spectrometry, and mass spectrometry, and the like.

(3) The pH of the water phase remained after extraction by ethyl acetate in the procedure of (2) above was adjusted to 2.0 using 2N hydrogen chloride aqueous solution. From this water phase α-methyl-β-mercaptopropionic acid was extracted using 400 ml of ethyl acetate. The same extraction procedure was repeated using the same amount of ethyl acetate. From the both ethyl acetate phases ethyl acetate was removed under a vacuum, and the residue was subjected to distillation at 3 mmHg to collect the fraction distilled at a temperature near 91° C. The fraction was optically active α-methyl-β-mercaptopropionic acid 4.2 gm {$[\alpha]_D^{25} = +26.5$ (C=3.0 methanol)}. This compound was identified by $C^{13}$ NMR, H-NMR, infrared spectrometry, and mass spectrometry, and the like.

EXAMPLE 2

(1) A culture medium in the amount of 100 ml, comprising 2% of peptone and 0.4% of yeast extract, and adjusted to pH 7.0 was sterilized. The strain *Microbacterium lacticum* ATCC 8180 was inoculated to the culture medium and cultured at 28° C. for 30 hours. The culture broth was centrifuged to collect the microorganism, to which 2 ml of physiological saline was added to obtain a suspension of the microorganism.

(2) Two (2) ml of the suspension of the microorganism prepared in (1) above was added to 100 ml of water containing 1 gm of d-α-methyl-β-mercaptopropionic acid methyl ester. The mixture was adjusted to pH 8.0 using 2N sodium hydroxide aqueous solution, and reacted to 30° C. for 3 hours. After the reaction, the same procedure as that carried out in Example 1 was followed to obtain 0.33 gm of optically active α-methyl-β-mercaptopropionic acid methyl ester and 0.40 gm of optically active α-methyl-β-mercaptopropionic acid. The optical rotations of these compounds are $[\alpha]_D^{25} = +33$ (C=1.05 methanol) and $[\alpha]_D^{25} = -25$ (C=3.0 methanol), respectively.

Each ethyl acetate solution obtained after the extraction procedure which contains optically active α-methyl-β-mercaptopropionic acid methyl ester or its asymmetrical isomer, optically active α-methyl-β-mercaptopropionic acid, was subjected to high performance liquid chromatography (HPLC) analysis under the conditions shown below. As a result, the peaks of the compounds for the both solutions showed almost the same pattern, demonstrating that both ethyl acetate solutions after extraction containing optically active α-methyl-β-mercaptopropionic acid methyl ester or its asymmetrical isomer, optically active α-methyl-β-mercaptopropionic acid, have an identical composition on HPLC.

HPLC Conditions

Column:
  Shodex KC-811 (manufactured by Showa Denko Co., Ltd.)
Flow rate:
  1.0 ml/min
Mobile phase:
  $8.5 \times 10^{-3}\%$ $HClO_4$ aqueous solution
Temperature:
  60° C.
Detection:
  U.V. 225 nm
Holding time:
  α-methyl-β-mercaptopropionic acid methyl ester: 17.0 min.
  α-methyl-β-mercaptopropionic acid: 15.0 min.

EXAMPLES 3–17

Media listed in Table 1 was sterilized, and microorganisms shown in Table 1 were inoculated in each 100 ml of the media and cultured at 28° C. The cultured microorganisms were collected according to the method described in Example 2 (1). Also, following the same procedure as in Example 2 (1), the reaction using 1.0 gm of dτ-α-methyl-β-mercaptopropionic acid methyl ester as substrate was carried out under the reaction conditions shown in Table 1 to obtain optically active α-methyl-β-mercaptopropionic acid methyl ester. The optical rotation of α-methyl-β-mercaptopropionic acid methyl ester thus obtained was measured and the results are shown in Table 1.

TABLE 1

| Examples | Strain of microorganism used | Culture conditions Media* | Time (hrs) | pH | Reaction conditions Time (hrs) | Temp. (°C.) | Rotation of the product ($[\alpha]_D^{25}$ C = 1.0, MeOH) | Optically active ester produced (gm) |
|---|---|---|---|---|---|---|---|---|
| No. 3 | *Bacillus laterosporus* ATCC 64 | No. 1 | 30 | 7.0 | 8 | 30 | −32 | 0.31 |
| No. 4 | *Flavobacterium ferrugineum* ATCC 13524 | No. 1 | 30 | 8.0 | 8 | 30 | −32 | 0.28 |
| No. 5 | *Alcaligenes faecalis* ATCC 15246 | No. 1 | 30 | 8.0 | 8 | 30 | +32 | 0.28 |
| No. 6 | *Pseudomonas piscicida* ATCC 15251 | No. 1 | 30 | 8.0 | 8 | 30 | −32 | 0.26 |
| No. 7 | *Caulobactor crescentus* ATCC 19089 | No. 1 | 30 | 8.0 | 8 | 30 | +32.5 | 0.29 |
| No. 8 | *Acinetobactor lwoffii* ATCC 21284 | No. 1 | 30 | 8.0 | 8 | 30 | −32 | 0.27 |
| No. 9 | *Candida utilis* ATCC 9226 | No. 2 | 70 | 8.0 | 8 | 30 | −32 | 0.26 |
| No. 10 | *Cryptococcus laurentii* ATCC 18803 | No. 2 | 70 | 7.0 | 8 | 30 | −32 | 0.22 |
| No. 11 | *Trichosporon cutaneum* IFO 0173 | No. 2 | 70 | 7.0 | 8 | 30 | −32.5 | 0.25 |
| No. 12 | *Rhodutorula minuta* IFO 0387 | No. 2 | 70 | 8.0 | 8 | 30 | +32 | 0.28 |
| No. 13 | *Cryptococcus albidus* ATCC 1320 | No. 2 | 70 | 8.0 | 8 | 30 | +32 | 0.23 |
| No. 14 | *Rhodotorula glutinis* IFO 0389 | No. 2 | 70 | 7.0 | 8 | 30 | +32.5 | 0.29 |
| No. 15 | *Sporidiobolus johnsonii* IFO 6903 | No. 2 | 70 | 7.0 | 8 | 30 | −32 | 0.30 |
| No. 16 | *Rhodosporidium toruloides* NRRL Y-1019 | No. 2 | 70 | 7.0 | 8 | 30 | −33 | 0.28 |
| No. 17 | *Sporobolomyces albo-* | No. 2 | 70 | 7.0 | 8 | 30 | −32 | 0.27 |

TABLE 1-continued

| Examples | Strain of microorganism used | Culture conditions Media* | Time (hrs) | pH | Reaction conditions Time (hrs) | Temp. (°C.) | Rotation of the product ($[\alpha]_D^{25}$ C = 1.0, MeOH) | Optically active ester produced (gm) |
|---|---|---|---|---|---|---|---|---|
| | rubescens NRRL Y-6683 | | | | | | | |

*Culture media
No. 1: media containing 2% of peptone and 0.4% of yeast extract (pH 7)
No. 2: media containing 2% of glucose, 0.5% of peptone, 0.3% of malt extract, and 0.3% of yeast extract (pH 6)

EXAMPLE 18

(1) Wet bacteria of the strain *Rhodotorula glutinis* IFO 0389 in the amount of 350 ml (weight: 35 gm on dry basis) which was obtained in the same manner as in Example 1 and 30 gm of powdery active carbon (Trade name: Shirosagi A; manufactured by Takeda Pharmaceutical Co., Ltd.) were homogeneously mixed. To this mixture 400 ml of 20% aqueous solution of PVA (a solution obtained by dissolving a commercial PVA with saponification value of 99.45 mol% and polymerization degree of 1700 in water) was added and homogeneously mixed. The mixture thus obtained was fed into an open mold with a square of 2×2 mm and 20 cm long using an injector, and air-dried at 45° C. for 3.5 hours to obtain molds containing cultured microorganism. These were cut into 2 mm cubes, air-dried at 50° C. for 16 hours to obtain immobilized mycelium.

(2) All of the immobilized mycelium was dissolved in 2,000 ml of water containing 20 gm of d-α-methyl-β-mercaptopropionic acid methyl ester, and the pH of the solution was adjusted to 7.0 using 2N aqueous solution of sodium hydroxide. The mixture was then reacted at 30° C. for 20 hours. Upon completion of the reaction, the reaction mixture was centrifuged to remove the microorganism, and unhydrolyzed α-methyl-β-mercaptopropionic acid methyl ester remaining in the filtrate was extracted using 400 ml of ethyl acetate. This extraction procedure was once more repeated using 400 ml of ethyl acetate. The ethyl acetate phases obtained by the extraction were collected, from which ethyl acetate was removed under a vacuum, and the residue was subjected to distillation at 8 mmHg to collect the fraction distilled at a temperature range of 52°–54° C. The fraction weighing 6.2 gm was optically active α-methyl-β-mercaptopropionic acid methyl ester $\{[\alpha]_D^{25} = -32$ (C=1.05 methanol)$\}$.

EXAMPLE 19

Three (3) gm of τ-α-methyl-β-mercaptopropionic acid methyl ester was dissolved in 300 ml of water. To this solution 100 U of esterase (derived from swine liver, manufactured by Sigma Co.,) was added. The mixture was reacted at a temperature of 30° C. for 20 hours, while controlling the pH at 7.0 by adding 2N sodium hydroxide aqueous solution. After the reaction, the reaction mixture was adjusted to pH 2.0 using 2N hydrogen chloride aqueous solution, and treated in the same manner as in in Example 1 (3) to obtain 2.6 gm of τ-α-methyl-β-mercaptopropionic acid. The compound had a rotation of $[\alpha]_D^{25} = -26.5$ (C=1.05 methanol).

REFERENCE EXAMPLE 1

*Bacillus subtilis var. niger* IFO 3108 was cultured according to the method described in Example 2 of Japanese Patent Laid-open No. 94091/1985 to obtain 7.0 gm of microorganism after washing. The enzymatic reaction as described in the Example 2 of Japanese Patent Laid-open No. 94091/1985 was conducted, except that instead of s-acetyl-β-mercaptoisobutyric acid 30 ml of α-methyl-β-mercaptopropionic acid methyl ester was used as substrate. As a result, almost all of the substrate, α-methyl-β-mercaptopropionic acid methyl ester, was hydrolyzed, and no α-methyl-β-mercaptopropionic acid methyl ester was found in the reaction mixture.

REFERENCE EXAMPLE 2

The enzymatic reaction as described in Example 2 of Japanese Patent Laid-open No. 94091/1985 was conducted, using 20 ml of α-methyl-β-mercaptopropionic acid methyl ester as substrate and 10 gm of lipase M-AP10 (manufactured by Amano Pharmaceutical Co., Ltd.). As a result, almost all of the substrate, α-methyl-β-mercaptopropionic acid methyl ester, was hydrolyzed, and no α-methyl-β-mercaptopropionic acid methyl ester was found in the reaction mixture.

REFERENCE EXAMPLES 3–6

Strains of microorganisms listed in Table 2 were cultured in culture media shown in Table 2. The reaction was carried out using α-methyl-β-mercaptopropionic acid methyl ester as substrate. The results are shown in Table 2.

TABLE 2

| Reference Examples | Strain of microorganism used | Culture-conditions Media* | Time (hrs) | pH | Reaction-conditions Time (hrs) | Temp. (°C.) | Product produced |
|---|---|---|---|---|---|---|---|
| No. 3 | *Bacillus subtilis* var. negar IFO 3180 | No. 1 | 30 | 7.0 | 8 | 30 | All substrate compound was hydrolyzed and did not found in the products. |
| No. 4 | *Bacillus subtilis* var. negar IFO 3180 | No. 2 | 30 | 7.0 | 8 | 30 | |
| No. 5 | *Pseudomonas fluorescence* IFO 3081 | No. 1 | 30 | 7.0 | 8 | 30 | |
| No. 6 | *Pseudomonas fluorescence* IFO 3081 | No. 2 | 30 | 7.0 | 8 | 30 | |

*Culture media
No. 1: media containing 2% of peptone and 0.4% of yeast extract
No. 2: media containing 1% of meat extract, 1% of peptone, and 0.5% of NaCl As evident from the above Examples and Reference Examples, according to the method of the present invention optical active isomers of mercapto compounds having asymmetrical centers can be efficiently prepared without protecting free mercapto groups which are unstable in the reaction.

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent is:

1. A process for preparing an optically active mercapto compound having the formula (A):

wherein $R_1$ is alkyl, R is hydrogen or alkyl, C* is an asymmetric carbon atom, and n is 1 or 2, comprising:
contacting a compound of the formula (B):

wherein $R_2$ is alkyl and $R_1$ and n are as defined above with a cultured product or a treated product thereof of a species of microorganism, said cultured product or treated product thereof having the capability of selectively hydrolyzing the ester bonds of an enantiomer of the compound of formula (B); and
separating said compound of formula (A) from the resulting mixture.

2. The process according to claim 1, wherein n in formulae (A) and (B) is 1.

3. The process according to claim 1, wherein $R^1$ in formulae (A) and (B) is a methyl group.

4. The process according to claim 1, wherein the microorganism having the ability of asymmetrically hydrolyzing ester bonds of said compound of the formula (B) is a member selected from the group consisting of genuses of Rhodotorula, Microbacterium, Bacillus, Alcaligenes, Flavobacterium, Acinetobactor, Pseudomonas, Candida, Caulobacter, Sporidiobolus, Cryptococcus, Trichosporon, Rhodosporidium, and Sporobolomyces.

5. The process according to claim 1, wherein the microorganism having the ability of asymmetrically hydrolyzing ester bond of said compound of formula (B) is a member selected from the group of strains consisting of *Rhodotorula glutinis, Rhodotorula minuta, Microbacterium lacticum, Bacillus laterosporus, Alcaligenes faecalis, Pseudomonas piscicida, Caulobacter crescentus, Flavobacterium ferrugineum, Acinetobactor lwoffii, Candida utilis, Sporidiobolus johnsonii, Cryptococcus laurentii, Cryptococcus albidus, Trichosporon cutaneum, Rhodosporidium toruloides,* and *Sporobolomyces albo-rubescens.*

6. The process according to claim 1, wherein the microorganism having the ability of asymmetrically hydrolyzing ester bonds of said compound of formula (B) is a member selected from the group of strains consisting of *Rhodotorula glutinis* IFO 0389, *Rhodotorula minuta* IFO 0387, *Microbacterium lacticum* ATCC 8180, *Bacillus laterosporus* ATCC 64, *Alcaligenes faecalis* ATCC 15246, *Pseudomonas piscicida* ATCC 15251, *Caulobacter crescentus* ATCC 19089, *Flavobacterium ferrugineum* ATCC 13524, *Acinetobactor lwoffii* ATCC 21284, *Candida utilis* ATCC 9226, *Sporidiobolus johnsonii* IFO 6903, *Cryptococcus laurentii* ATCC 18803, *Cryptococcus albidus* IFO 1320, *Trichosporon cutaneum* IFO 0173, *Rhodosporidium toruloides* NRRL Y-1019, and *Sporobolomyces albo-rubescens* NRRL Y-6683.

* * * * *